US012083209B2

(12) United States Patent
Hashimoto et al.

(10) Patent No.: US 12,083,209 B2
(45) Date of Patent: Sep. 10, 2024

(54) ORAL CARE COMPOSITION

(71) Applicant: SUNSTAR AMERICAS, INC., Schaumburg, IL (US)

(72) Inventors: Kana Hashimoto, Mount Prospect, IL (US); Toru Saito, Buffalo Grove, IL (US)

(73) Assignee: SUNSTAR AMERICAS, INC., Schaumburg, IL (US)

( * ) Notice: Subject to any disclaimer, the term of this patent is extended or adjusted under 35 U.S.C. 154(b) by 0 days.

(21) Appl. No.: 17/174,698

(22) Filed: Feb. 12, 2021

(65) Prior Publication Data

US 2021/0251870 A1 Aug. 19, 2021

Related U.S. Application Data

(60) Provisional application No. 62/978,098, filed on Feb. 18, 2020.

(51) Int. Cl.

| | |
|---|---|
| ***A61K 8/49*** | (2006.01) |
| ***A61K 8/44*** | (2006.01) |
| ***A61K 8/73*** | (2006.01) |
| ***A61K 8/92*** | (2006.01) |
| ***A61Q 11/00*** | (2006.01) |

(52) U.S. Cl.

CPC ............ *A61K 8/4926* (2013.01); *A61K 8/442* (2013.01); *A61K 8/731* (2013.01); *A61K 8/922* (2013.01); *A61Q 11/00* (2013.01); *A61K 2800/30* (2013.01); *A61K 2800/48* (2013.01)

(58) Field of Classification Search

CPC ........ A61K 8/922; A61K 8/731; A61K 8/442; A61K 8/4926; A61K 2800/30; A61K 2800/48; A61Q 11/00

See application file for complete search history.

(56) References Cited

U.S. PATENT DOCUMENTS

| | | | |
|---|---|---|---|
| 4,233,288 | A | 11/1980 | Cornell |
| 4,945,087 | A | 7/1990 | Talwar et al. |
| 5,266,306 | A | 11/1993 | Ohtsuki et al. |
| 5,496,558 | A | 3/1996 | Napolitano et al. |
| 5,541,165 | A | 7/1996 | Turgeon |
| 5,560,906 | A | 10/1996 | Scodari et al. |
| 5,658,554 | A | 8/1997 | Fisher et al. |
| 6,066,345 | A | 5/2000 | de Cock |
| 6,117,417 | A | 9/2000 | Wicks et al. |
| 6,159,459 | A | 12/2000 | Hunter et al. |
| 6,177,064 | B1 | 1/2001 | de Troostembergh et al. |
| 6,355,229 | B1 | 3/2002 | Adamy |
| 6,471,948 | B1 | 10/2002 | Adamy et al. |
| 6,579,513 | B1 | 6/2003 | Tashjian et al. |
| 6,656,920 | B2 | 12/2003 | Fox et al. |
| 6,706,781 | B2 | 3/2004 | Rajaiah et al. |
| 6,828,308 | B2 | 12/2004 | Mastradonato et al. |
| 7,198,779 | B2 | 4/2007 | Pinol et al. |
| 7,501,452 | B2 | 3/2009 | Troha et al. |
| 7,879,877 | B2 | 2/2011 | Nagamoto et al. |
| 7,910,089 | B2 | 3/2011 | Uotani et al. |
| 8,075,924 | B2 | 12/2011 | Loewy et al. |
| 8,221,724 | B2 | 7/2012 | Hughes et al. |
| 8,287,842 | B2 | 10/2012 | Katou et al. |
| 8,367,650 | B2 | 2/2013 | Desjonqueres |
| 8,444,958 | B2 | 5/2013 | Kamasaka et al. |
| 8,506,937 | B2 | 8/2013 | Kho et al. |
| 8,540,970 | B2 | 9/2013 | Rodriguez-Vilaboa |
| 8,658,139 | B1 | 2/2014 | Cutler |
| 8,858,920 | B2 | 10/2014 | Robinson et al. |
| 9,044,466 | B2 | 6/2015 | Cohen et al. |
| 9,138,428 | B2 | 9/2015 | Cohen et al. |
| 9,149,454 | B2 | 10/2015 | Cooper et al. |
| 9,192,565 | B2 | 11/2015 | Vogt et al. |
| 9,198,844 | B2 | 12/2015 | Brisley |
| 9,241,885 | B2 | 1/2016 | Roberge et al. |
| 2002/0168334 | A1 | 11/2002 | Jacob et al. |
| 2003/0232858 | A1 | 12/2003 | Barker et al. |
| 2004/0170576 | A1 | 9/2004 | Grainger et al. |
| 2005/0100601 | A1 | 5/2005 | Capps |
| 2005/0244346 | A1 | 11/2005 | Nakao et al. |
| 2005/0250821 | A1 | 11/2005 | Sewalt et al. |
| 2006/0094643 | A1 | 5/2006 | Svirkin et al. |
| 2006/0134011 | A1 | 6/2006 | Shanahan |
| 2006/0134020 | A1 | 6/2006 | Robinson et al. |
| 2006/0204551 | A1 | 9/2006 | Manley et al. |
| 2007/0031561 | A1 | 2/2007 | Lakkis et al. |

(Continued)

FOREIGN PATENT DOCUMENTS

| | | |
|---|---|---|
| CN | 101778618 A | 7/2010 |
| CN | 101780016 A | 7/2010 |

(Continued)

OTHER PUBLICATIONS

Takahashi et al., "Feasibility of Emotion Recognition from Breath Gas Information", Proceedings of the 2008 IEEE/ASME International Conference on Advanced Intelligent Mechatronics Jul. 2-5, 2008, Xi'an, China. (Year: 2008).*

Ialenti et al., "Hyaluronic acid inhibits polycation induced cellular responses," Mediators of Inflammation, 1994, vol. 3, Issue 4, pp. 287-289.

Jia et al., "New Formulation of Drug Controlled Release," Chemical Industry Press, 2005, pp. 242-244 (6 pages including translation).

Rölla et al., "Experiments with a toothpaste containing polydimethylsiloxan/triclosan," Scandinavian Journal of Dental Research, 1993, vol. 101, No. 3, pp. 130-132.

(Continued)

*Primary Examiner* — Lezah Roberts

(74) *Attorney, Agent, or Firm* — Michael Best & Friedrich LLP

(57) ABSTRACT

An oral care composition including greater than 0.0% of an antimicrobial agent that is cetylpyridinium chloride (CPC), a cationic surfactant, an emulsifier, and less than 0.5% by weight of a thickener, such as hydroxyethylcellulose.

18 Claims, No Drawings

(56) References Cited

U.S. PATENT DOCUMENTS

| | | | |
|---|---|---|---|
| 2007/0274929 | A1 | 7/2007 | Alexander et al. |
| 2008/0118446 | A1 | 5/2008 | Jablow |
| 2008/0247972 | A1 | 10/2008 | Conceicao |
| 2008/0317703 | A1 | 12/2008 | Kawa et al. |
| 2009/0068122 | A1 | 3/2009 | Pilch et al. |
| 2009/0081294 | A1 | 3/2009 | Gin et al. |
| 2009/0104128 | A1 | 4/2009 | Haley |
| 2009/0252690 | A1 | 10/2009 | Behan et al. |
| 2009/0253804 | A1 | 10/2009 | Marcy et al. |
| 2010/0022471 | A1 | 1/2010 | Hanifl et al. |
| 2010/0098791 | A1 | 4/2010 | Rodriguez-Vilaboa |
| 2010/0216830 | A1 | 8/2010 | Iyoha et al. |
| 2011/0014136 | A1 | 1/2011 | Kohli et al. |
| 2011/0020417 | A1 | 1/2011 | Takeyama et al. |
| 2011/0104080 | A1 | 5/2011 | Salloum et al. |
| 2011/0104081 | A1 | 5/2011 | Scott et al. |
| 2011/0171342 | A1 | 7/2011 | Phillips, III et al. |
| 2011/0189110 | A1 | 8/2011 | Kohli et al. |
| 2012/0003162 | A1 | 1/2012 | Mordas et al. |
| 2012/0003163 | A1 | 1/2012 | Mordas et al. |
| 2013/0236400 | A1 | 9/2013 | Lewus et al. |
| 2013/0251772 | A1 | 9/2013 | Chopra et al. |
| 2013/0272971 | A1 | 10/2013 | Pimenta et al. |
| 2013/0295041 | A1 | 11/2013 | Kawa et al. |
| 2013/0344011 | A1 | 12/2013 | Ramji et al. |
| 2013/0344120 | A1 | 12/2013 | Scott et al. |
| 2014/0099347 | A1 | 4/2014 | Prencipe |
| 2014/0155457 | A1 | 6/2014 | Nho et al. |
| 2014/0187629 | A1 | 7/2014 | Walker et al. |
| 2014/0271497 | A1 | 9/2014 | Morgan |
| 2014/0286880 | A1 | 9/2014 | Vogt et al. |
| 2015/0030547 | A1 | 1/2015 | Liao et al. |
| 2015/0231060 | A1 | 8/2015 | Okay |
| 2015/0320701 | A1 | 11/2015 | Shigeki |
| 2015/0335549 | A1 | 11/2015 | Patel et al. |
| 2015/0366794 | A1 | 12/2015 | Cooper et al. |
| 2016/0008250 | A1 | 1/2016 | Cohen et al. |
| 2016/0374352 | A1 | 12/2016 | Modak et al. |

FOREIGN PATENT DOCUMENTS

| | | | |
|---|---|---|---|
| CN | 101999990 | A | 4/2011 |
| CN | 102639100 | A | 8/2012 |
| CN | 103154726 | A | 6/2013 |
| CN | 103385821 | A | 11/2013 |
| EA | 001191 | B1 | 12/2000 |
| EP | 0413427 | A2 | 2/1991 |
| EP | 2100590 | B1 | 10/2017 |
| GB | 2348370 | A | 10/2000 |
| GB | 2354709 | A | 4/2001 |
| JP | H01153620 | A | 6/1989 |
| JP | H01246214 | A | 10/1989 |
| JP | H0259513 | A | 2/1990 |
| JP | H02169514 | A | 6/1990 |
| JP | H03151317 | A | 6/1991 |
| JP | H04173728 | A | 6/1992 |
| JP | H04202121 | A | 7/1992 |
| JP | H06239723 | A | 8/1994 |
| JP | H0725734 | A | 1/1995 |
| JP | H0725735 | A | 1/1995 |
| JP | H07133222 | A | 5/1995 |
| JP | H0812542 | A | 1/1996 |
| JP | H0848622 | A | 2/1996 |
| JP | H0825863 | B2 | 3/1996 |
| JP | H08217653 | A | 8/1996 |
| JP | H08259444 | A | 10/1996 |
| JP | H08268854 | A | 10/1996 |
| JP | H08268855 | A | 10/1996 |
| JP | 2603465 | B2 | 4/1997 |
| JP | H0995457 | A | 4/1997 |
| JP | H1112142 | A | 1/1999 |
| JP | H1112168 | A | 1/1999 |
| JP | H1149625 | A | 2/1999 |
| JP | H1179961 | A | 3/1999 |
| JP | H11116452 | A | 4/1999 |
| JP | H11209254 | A | 8/1999 |
| JP | 2000129299 | A | 5/2000 |
| JP | 2001072562 | A | 3/2001 |
| JP | 2001247446 | A | 9/2001 |
| JP | 2001342500 | A | 12/2001 |
| JP | 2002370956 | A | 12/2002 |
| JP | 2003034619 | A | 2/2003 |
| JP | 2003113059 | A | 4/2003 |
| JP | 2006016309 | A | 1/2006 |
| JP | 2006151876 | A | 6/2006 |
| JP | 2006306768 | A | 11/2006 |
| JP | 2007008843 | A | 1/2007 |
| JP | 2007084471 | A | 4/2007 |
| JP | 2008120753 | A | 5/2008 |
| JP | 2008143870 | A | 6/2008 |
| JP | 2008156288 | A | 7/2008 |
| JP | 2009062285 | A | 3/2009 |
| JP | 2009107989 | A | 5/2009 |
| JP | 2010143843 | A | 7/2010 |
| JP | 2011073970 | A | 4/2011 |
| JP | 2011073996 | A | 4/2011 |
| JP | 2011132169 | A | 7/2011 |
| JP | 2011140454 | A | 7/2011 |
| JP | 2011148706 | A | 8/2011 |
| JP | 2011153138 | A | 8/2011 |
| JP | 2011173873 | A | 9/2011 |
| JP | 2012012303 | A | 1/2012 |
| JP | 2012111732 | A | 6/2012 |
| JP | 2012121833 | A | 6/2012 |
| JP | 2012136504 | * | 7/2012 |
| JP | 2012158580 | A | 8/2012 |
| JP | 2012201632 | A | 10/2012 |
| JP | 2012214402 | A | 11/2012 |
| JP | 2013035760 | A | 2/2013 |
| KR | 20000060197 | A | 10/2000 |
| KR | 20040081936 | A | 9/2004 |
| KR | 20080049177 | A | 6/2008 |
| KR | 20110074232 | A | 6/2011 |
| KR | 20130107397 | A | 10/2013 |
| MX | 2013007035 | A | 9/2013 |
| RU | 2009114589 | A | 12/2010 |
| RU | 2432149 | C2 | 10/2011 |
| RU | 2011117012 | A | 1/2013 |
| RU | 2486891 | C2 | 7/2013 |
| SI | 910333 | | 4/2003 |
| WO | WO8907932 | A1 | 9/1989 |
| WO | WO9311754 | A1 | 6/1993 |
| WO | WO9418939 | A1 | 9/1994 |
| WO | WO02080946 | A1 | 10/2002 |
| WO | WO03002056 | A2 | 1/2003 |
| WO | WO2004071475 | A1 | 8/2004 |
| WO | WO2005039518 | A1 | 5/2005 |
| WO | WO2007009879 | A1 | 1/2007 |
| WO | WO2007066497 | A1 | 6/2007 |
| WO | WO2007134335 | A2 | 11/2007 |
| WO | WO2008013740 | A2 | 1/2008 |
| WO | WO2009032406 | A1 | 3/2009 |
| WO | WO2009098531 | A1 | 8/2009 |
| WO | WO2009106963 | A2 | 9/2009 |
| WO | WO2009117644 | A1 | 9/2009 |
| WO | WO2009135867 | A1 | 11/2009 |
| WO | WO2010121081 | A1 | 10/2010 |
| WO | WO2012021419 | A2 | 2/2012 |
| WO | WO2013062424 | A1 | 5/2013 |
| WO | WO2013096427 | A2 | 6/2013 |
| WO | WO2014165226 | A2 | 10/2014 |

OTHER PUBLICATIONS

International Search Report and Written Opinion for Application No. PCT/US2021/017924 dated Apr. 26, 2021 (15 pages).

Database GNPD Mintel; Nov. 28, 2018, "Regular Mouthwash", XP093122935, Database accession No. 6166865 (3 pages).

European Patent Office Supplementary Search Report for Application No. 21756589 dated Feb. 12, 2024 (11 pages).

* cited by examiner

ORAL CARE COMPOSITION

CROSS-REFERENCE TO RELATED APPLICATIONS

This application claims the benefit of U.S. Provisional Patent Application No. 62/978,098, filed Feb. 18, 2020, which is incorporated by reference.

FIELD

The present invention relates to a liquid oral care composition such as a mouthwash or mouth spray.

SUMMARY

One embodiment discloses a liquid oral care composition including greater than 0.0% of an antimicrobial agent that is cetylpyridinium chloride (CPC), a cationic surfactant, an emulsifier, and less than 0.5% by weight of a thickener, such as hydroxyethylcellulose.

Another embodiment discloses a liquid oral care composition including 0.01% by weight to 0.4% by weight cetylpyridinium chloride (CPC), 0.005% by weight to 0.05% by weight PCA ethyl cocoyl arginate, 0.05% by weight to 2% by weight PEG-60 hydrogenated castor oil, and less than 0.5% by weight of hydroxyethylcellulose.

Another embodiment discloses a method of treating teeth including applying a liquid oral care composition including greater than 0.0% of an antimicrobial agent that is cetylpyridinium chloride (CPC), a cationic surfactant, an emulsifier, and less than 0.5% by weight of a thickener, such as hydroxyethylcellulose. In another embodiment, the cationic surfactant is PCA ethyl cocoyl arginate and the emulsifier is PEG-60 hydrogenated castor oil. In another embodiment, the composition includes 0.01% by weight to 0.4% by weight CPC, 0.005% by weight to 0.05% by weight PCA ethyl cocoyl arginate, 0.05% by weight to 2% by weight PEG-60 hydrogenated castor oil, and no more than 0.2% by weight hydroxyethylcellulose. In another embodiment, the composition includes 0.02% by weight to 0.1% by weight CPC, 0.005% by weight to 0.02% by weight PCA ethyl cocoyl arginate, 0.1% by weight to 0.5% by weight PEG-60 hydrogenated castor oil, and no more than 0.2% by weight hydroxyethylcellulose. In another embodiment, the composition includes 0.05% by weight to 0.1% by weight CPC, 0.005% by weight to 0.02% by weight PCA ethyl cocoyl arginate, 0.1% by weight to 0.5% by weight PEG-60 hydrogenated castor oil, and 0.1% by weight to 0.2% by weight hydroxyethylcellulose. In some embodiments, the composition is a mouthwash or mouth spray.

DETAILED DESCRIPTION

Dental plaque is formed by adsorption and propagation of harmful intraoral bacteria, such as *Streptococcus mutans* ("*S mutans*"), Aggregatibacter *actinomycetemcomitans, Porphyromonas gingivalis, Prevotella intermedia*, and *Treponema denticola* and the like on the surfaces of teeth. Dental plaque is a known cause of dental caries and gingivitis or periodontitis. Therefore, it is important to remove dental plaque and to prevent adhesion of it (plaque control) for oral sanitation.

One embodiment of an oral composition (e.g., a mouthwash or a mouth spray) comprises an antimicrobial agent, a cationic surfactant, an emulsifier, and a thickener. Preferably, the antimicrobial agent is cetylpyridinium chloride (CPC), the cationic surfactant is PCA ethyl cocoyl arginate, the emulsifier is PEG-60 hydrogenated castor oil, and the thickener is hydroxyethylcellulose. The oral care composition may optionally include additional surfactants, soothing or desensitizing agents, flavoring agents, sweetening agents, humectant agents, coloring agents, additional antimicrobial agents, binders or thickening agents, fluoride, preservatives, and water. The oral care composition, however, does not include an anionic surfactant because the anionic molecules of the anionic surfactant reduces the efficacy of CPC.

CPC has positively charged molecules that interact with negatively charged anionic sites on the cell walls of bacteria. Positively charged CPC can also bind to a tooth surface, which is also negatively charged. CPC can bind with and remain on the tooth surface for a long term. CPC can make an antimicrobial veil on the teeth and thereby help to prevent attachment of bacteria and accumulation of biofilm. Accordingly, CPC can help prevent dental plaque and dental caries by attacking bacteria and adsorbing to the oral mucosa or the surfaces of the teeth. However, when CPC is used in a formulation, other components of the formulation can reduce the ability of CPC to act as an antimicrobial agent. First, CPC is positively charged, so other negatively charged material in a formulation (e.g., anionic molecules) can react with the positively charged CPC molecules, which reduces the activity of CPC with bacteria and tooth surfaces thereby reducing the activity of CPC as an antimicrobial agent. Second, CPC also has characteristics of a surfactant. Therefore, CPC can form a micelle with other surfactants in a formulation. The formation of a micelle may interfere with the ability of CPC to attack the bacteria thereby reduce the antimicrobial activity.

The use of the cationic surfactant and the emulsifier in a formulation with CPC increases the antimicrobial effect of CPC in attacking bacteria and preventing dental plaque and dental caries. The cationic surfactant in the formulation competes with CPC to bind to anionic molecules in the formulation. That is, the cationic molecules of the cationic surfactant bind with anionic molecules in the formulation thereby preventing CPC from binding to anionic molecules in formulation. Accordingly, the CPC is free to attack bacteria and adsorb to the oral mucosa and surfaces of teeth. In the preferred embodiment, the cationic surfactant is PCA ethyl cocoyl arginate, which is an amino acid-based cationic surfactant derived from L-arginine, DL-pyrrolidone carboxylic acid and fatty acid. In other or additional embodiments, other suitable cationic surfactant may be used. These may include one or more of quaternary ammonium salts (e.g., benzalkonium chloride, benzethonium chloride, dimethyldioctadecylammonium chloride, dtearyldimethylbenzyl ammonium chloride, stearyltrimethylammonium chloride, cetyltrimethylaminium chloride, lauryltrimethylammonium chloride), bisbiguanides (e.g., chlorhexidine chloride, chlorhexidine acetate, chlorhexidine gluconate, alexidine hydrochloride, alexidine acetate, alexidine gluconate), or N-long-chain acyl basic amino acid lower alkyl esters or the salts thereof (e.g., pyrrolidonecaboxylic acid salt of N-Lauryl L-Arginine ethyl ester, pyrrolidonecaboxylic acid salt of N-Lauryl L-Arginine methyl ester, caboxylic acid salt of N-Palmitoyl L-Lysine methyl ester, hydrochloric acid salt of N-Cocoyl L-Arginine methyl ester, or laurylpyridinium chloride).

Emulsifiers are surfactants and are typically used to help dissolution of oil (e.g., flavor oil) in water. Emulsifiers therefore form a micelle with CPC when used together in a formulation. The structure of the micelle, which is determined based on the structure of the emulsifier (i.e., surfactant), determines the level of CPC inhibition. The structure of the micelle that results from the use of a poly(oxyethylene) hydrogenated castor oil that has an average molar number of ethylene oxide units added of 35 to 100 moles has been shown to be most effective in reducing the level of CPC inhibition. Moreover, in the preferred embodiment, the emulsifier is PEG-60 hydrogenated castor oil.

In addition to making the oral care composition thicker, the thickener in the formulation helps the oral care composition to stay on the gum tissue. The thickener also gives the oral care composition its moisturizing and gentle finish. In a preferred embodiment, the thickener is hydroxyethylcellulose, which is a polymer. Hydroxyethylcellulose is particularly comfortable for users with dry mouth or a generally sensitive mouth. The amount of hydroxyethylcellulose in the formulation is important because too much hydroxyethylcellulose can reduce the antimicrobial activity of CPC. It is believed that less hydroxyethylcellulose in the formulation shows a higher antibacterial effect than higher amounts of hydroxyethylcellulose. Other suitable thickeners may additionally or alternatively be used, such as nonionic polymers (e.g., methylcellulose, hydroxypropyl methylcellulose, hydroxypropylcellulose, crystsalline cellulose, microcrystalline cellulose, polyvinylpyrroridone) or cationic polymers (e.g., cationic guar gum derivatives and cationized xanthan gum).

The CPC is greater than 0.0% by weight, and in some embodiments, the CPC may measure between 0.01% and 0.4% by weight. In some embodiment, the CPC measures 0.02% by weight to 0.1% by weight. In some embodiments, the CPC measures 0.06% by weight to 0.1% by weight. In some embodiments, for example, the CPC may measure 0.05% by weight, 0.075% by weight, or 0.1% by weight. In some embodiments, the PCA ethyl cocoyl arginate measures 0.005% by weight to 0.05% by weight. In some embodiments, the PCA ethyl cocoyl arginate measures 0.005% by weight to 0.02% by weight. In some embodiments, the PCA ethyl cocoyl arginate measures 0.008% by weight to 0.012% by weight. In some embodiments, for example, the PCA ethyl cocoyl arginate may measure 0.005% by weight, 0.01% by weight, or 0.02% by weight. In some embodiments, the PEG-60 hydrogenated castor oil measures 0.05% by weight to 2% by weight. In some embodiments, the PEG-60 hydrogenated castor oil measures 0.1% by weight to 0.5% by weight. In some embodiments, the PEG-60 hydrogenated castor oil measures 0.12% by weight to 0.2% by weight. In some embodiments, for example, the PEG-60 hydrogenated castor oil may measure 0.1% by weight, 0.15% by weight, 0.2% by weight, 0.3% by weight, or 0.5% by weight. In some embodiments, the hydroxyethylcellulose may be less than 0.5% by weight. In some embodiments, the hydroxyethylcellulose may be not more than 0.3% by weight. In some embodiments, the hydroxyethylcellulose may be not more than 0.2% by weight. In some embodiments, for example, the hydroxyethylcellulose may measure 0.1% by weight or 0.2 by weight.

In one embodiment, the CPC may measure 0.01% by weight to 0.4% by weight, the PCA ethyl cocoyl arginate measures 0.005% by weight to 0.05% by weight, the PEG-60 hydrogenated castor oil measures 0.05% by weight to 2% by weight, and the hydroxyethylcellulose measures not more than 0.3% by weight. In another embodiment, the CPC measures 0.02% by weight to 0.1% by weight, the PCA ethyl cocoyl arginate measures 0.005% by weight to 0.02% by weight, the PEG-60 hydrogenated castor oil measures 0.1% by weight to 0.5% by weight, and the hydroxyethylcellulose measures not more than 0.2% by weight. In another embodiment, the CPC measures 0.06% by weight to 0.1% by weight, the PCA ethyl cocoyl arginate measures 0.008% by weight to 0.012% by weight, the PEG-60 hydrogenated castor oil measures 0.12% by weight to 0.2% by weight, and the hydroxyethylcellulose measures not more than 0.2% by weight.

The oral care compositions discussed herein may be prepared by any suitable method.

The results of the following experiments show an antibacterial effect and usability of the various formulations. For each experiment, the antibacterial effect is tested using a first base having an array of wells and a second base having an array of hydroxyapatite coated pegs. In this experiment, the first base included 96 wells and the second base included 96 pegs. Each of the hydroxyapatite coated pegs is positioned within a single well. First, the hydroxyapatite coated pegs are soaked in sterilized saliva for one hour to initiate acquired salivary pellicle formation. Then the hydroxyapatite coated pegs are washed with deionized water for one minute. Thereafter six of the hydroxyapatite coated pegs are soaked in each test sample (disclosed in the tables below) for two minutes. The hydroxyapatite coated pegs are again washed with deionized water for one minute, three times. Then *S mutans* in a brain heart infusion medium (BD) having 5% sucrose is applied to the wells and cultured for 24 hours in aerobic condition at 37.0° C. Finally, each biofilm is dissolved with 200 μL 1N NaOH. The amount of *S mutans* adsorbed on the hydroxyapatite coated of each peg is measured using UV-vis spectrophotometric optical density at a wavelength of 550 nm ($OD_{550}$). The OD measurement is converted into a number representing the amount of *S mutans* in the remaining biofilm on the respective peg. Thereafter, an average amount of *S mutans* in the remaining biofilm after being treated with each sample was determined by taking an average of the data points for each of the six pegs used for each sample.

Also, the usability is tested for taste (e.g., bitterness) and texture (e.g., thickness) to evaluate usability. In particular, each of the test samples was subjected to an organoleptic test administered by trained scientists in a blind trial.

Experiment 1

Experiment 1 used the tests above to determine the antibacterial efficacy and usability of two emulsifiers. All concentrations are measured in percent by weight. In particular, Experiment 1 tested whether PEG-40 hydrogenated castor oil or PEG-60 hydrogenated castor oil has better antibacterial effect and usability. As shown in Table 1, below, Sample 2 including PEG-60 hydrogenated castor oil had a greater antimicrobial effect than PEG-40 hydrogenated castor oil because less bacteria resulted. The taste for both was favorable.

TABLE 1

| | Sample 1 | Sample 2 |
|---|---|---|
| CPC | 0.075 | 0.075 |
| PEG-40 hydrogenated castor oil | 0.15 | 0 |
| PEG-60 hydrogenated castor oil | 0 | 0.15 |
| PCA ethyl cocoyl arginate | 0.01 | 0.01 |

TABLE 1-continued

| | Sample 1 | Sample 2 |
|---|---|---|
| Hydroxyethylcellulose | 0.2 | 0.2 |
| S mutans in the remaining biofilm on the peg (Number of bacteria calculated from the OD) | $5.23 \times 10^8$ | $3.18 \times 10^8$ |
| Taste | Good | Good |

Experiment 2

Experiment 2 used the tests above to determine the antibacterial efficacy and usability of different concentrations of PCA ethyl cocoyl arginate. All concentrations are measured in percent by weight. As shown in Table 2, below, Sample 4 including 0.005% PCA ethyl cocoyl arginate had a greater antimicrobial effect than the samples having other concentrations because less bacteria resulted. Samples 5-8 including 0.01%, 0.02%, 0.05%, and 0.1% PCA ethyl cocoyl arginate, respectively, had a greater antimicrobial effect than Sample 3 having 0.0025% PCA ethyl cocoyl arginate because less bacteria resulted. Sample 8 having 0.1% PCA ethyl cocoyl arginate is not usable, however, because it has a bad or bitter taste.

TABLE 2

| | Sample 3 | Sample 4 | Sample 5 | Sample 6 | Sample 7 | Sample 8 |
|---|---|---|---|---|---|---|
| CPC | 0.075 | 0.075 | 0.075 | 0.075 | 0.075 | 0.075 |
| PEG-60 hydrogenated castor oil | 0.15 | 0.15 | 0.15 | 0.15 | 0.15 | 0.15 |
| PCA ethyl cocoyl arginate | 0.0025 | 0.005 | 0.01 | 0.02 | 0.05 | 0.1 |
| Hydroxyethylcellulose | 0.2 | 0.2 | 0.2 | 0.2 | 0.2 | 0.2 |
| S mutans in the remaining biofilm on the peg (Number of bacteria calculated from the OD) | $4.063 \times 10^8$ | $2.88 \times 10^8$ | $3.18 \times 10^8$ | $3.18 \times 10^8$ | $3.18 \times 10^8$ | $3.18 \times 10^8$ |
| Taste | Good | Good | Good | Good | Good | Bad (bitter) |

Experiment 3

Experiment 3 used the tests above to determine the antibacterial efficacy and usability of different concentrations of hydroxyethylcellulose. All concentrations are measured in percent by weight. As shown in Table 3, below, Sample 10 having a greater amount of hydroxyethylcellulose had a lesser antimicrobial effect than Sample 9 having less hydroxyethylcellulose. Also, Sample 10 was too thick and therefore not conducive for being used as a liquid oral composition.

TABLE 3

| | Sample 9 | Sample 10 |
|---|---|---|
| CPC | 0.075 | 0.075 |
| PEG-60 hydrogenated castor oil | 0.15 | 0.15 |
| PCA ethyl cocoyl arginate | 0.05 | 0.05 |
| Hydroxyethylcellulose | 0.2 | 0.5 |
| S mutans in the remaining biofilm on the peg (Number of bacteria calculated from the OD) | $2.88 \times 10^8$ | $4.34 \times 10^8$ |
| Taste | Good | Bad (too thick) |

Exemplary combinations of CPC, PCA ethyl cocoyl arginate, PEG-60 hydrogenated castor oil, and hydroxyethylcellulose in a formulation for an oral composition are given in the table below.

TABLE 4

| | Combination 1 | Combination 2 | Combination 3 | Combination 4 |
|---|---|---|---|---|
| Cetylpyridinium chloride (CPC) | 0.05 | 0.05 | 0.05 | 0.075 |
| PEG-60 hydrogenated castor oil | 0.15 | 0.2 | 0.3 | 0.1 |
| PCA ethyl cocoyl arginate | 0.01 | 0.01 | 0.005 | 0.02 |
| Hydroxyethylcellulose | 0.2 | 0.1 | 0.1 | 0.1 |

TABLE 5

| | Combination 5 | Combination 6 | Combination 7 | Combination 8 |
|---|---|---|---|---|
| Cetylpyridinium chloride (CPC) | 0.075 | 0.075 | 0.1 | 0.1 |
| PEG-60 hydrogenated castor oil | 0.15 | 0.2 | 0.15 | 0.5 |
| PCA ethyl cocoyl arginate | 0.01 | 0.01 | 0.01 | 0.02 |
| Hydroxyethylcellulose | 0.2 | 0.2 | 0.2 | 0.1 |

Although the invention has been described in detail with reference to certain preferred embodiments, variations and modifications exist within the scope and spirit of the invention.

What is claimed is:

1. A liquid oral composition comprising:

0.01% by weight to 0.4% by weight of an antimicrobial agent that is cetylpyridinium chloride (CPC);

0.005% by weight to 0.05% by weight of a cationic surfactant that is 2-pyrrolidone-5-carboxylic acid (PCA) ethyl cocoyl arginate;

0.05% by weight to 2% by weight of an emulsifier that is a poly(oxyethylene) hydrogenated castor oil that has an average molar number of ethylene oxide units added of 35 to 100 moles; and 0.1% by weight to 0.3% by weight of a thickener that is a non-ionic polymer.

2. The composition of claim 1, wherein the composition includes 0.02% by weight to 0.1% by weight CPC.

3. The composition of claim 1, wherein the composition includes 0.005% by weight to 0.02% by weight PCA ethyl cocoyl arginate.

4. The composition of claim 1, wherein the emulsifier is PEG-60 hydrogenated castor oil.

5. The composition of claim 4, wherein the composition includes 0.1% by weight to 0.5% by weight PEG-60 hydrogenated castor oil.

6. The composition of claim 1, wherein the thickener is hydroxyethylcellulose.

7. The composition of claim 1, wherein the composition includes one or more additional surfactants, soothing agents, desensitizing agents, flavoring agents, sweetening agents, humectant agents, coloring agents, antimicrobial agents, binders, thickening agents, fluoride, preservatives, and water.

8. The composition of claim 1, wherein the composition does not include an anionic surfactant.

9. The composition of claim 1, wherein the composition is a mouthwash or mouth spray.

10. The composition of claim 1, wherein, the emulsifier is PEG-60 hydrogenated castor oil, and the thickener is hydroxyethylcellulose, and wherein the composition includes 0.05% by weight to 0.1% by weight CPC, 0.005% by weight to 0.02% by weight PCA ethyl cocoyl arginate, 0.1% by weight to 0.5% by weight PEG-60 hydrogenated castor oil, and 0.1% by weight to 0.2% by weight hydroxyethylcellulose.

11. A liquid oral composition comprising:

0.01% by weight to 0.4% by weight cetylpyridinium chloride (CPC);

0.005% by weight to 0.05% by weight 2-pyrrolidone-5-carboxylic acid (PCA) ethyl cocoyl arginate;

0.05% by weight to 2% by weight PEG-60 hydrogenated castor oil; and 0.1% by weight to 0.3% by weight of hydroxyethylcellulose.

12. The composition of claim 11, wherein the composition includes 0.02% by weight to 0.1% by weight CPC, 0.005% by weight to 0.02% by weight PCA ethyl cocoyl arginate, and 0.1% by weight to 0.5% by weight PEG-60 hydrogenated castor oil.

13. The composition of claim 11, wherein the composition includes 0.05% by weight to 0.1% by weight CPC, 0.005% by weight to 0.02% by weight PCA ethyl cocoyl arginate, 0.1% by weight to 0.5% by weight PEG-60 hydrogenated castor oil, and 0.1% by weight to 0.2% by weight hydroxyethylcellulose.

14. The composition of claim 11, wherein the composition includes one or more additional surfactants, soothing agents, desensitizing agents, flavoring agents, sweetening agents, humectant agents, coloring agents, antimicrobial agents, binders, thickening agents, fluoride, preservatives, and water.

15. The composition of claim 11, wherein the composition does not include an anionic surfactant.

16. The composition of claim 11, wherein the composition is a mouthwash or mouth spray.

17. A method of treating teeth comprising:

applying a liquid oral composition to an oral cavity, the liquid oral composition including 0.01% by weight to 0.4% by weight of an antimicrobial agent that is cetylpyridinium chloride (CPC);

0.005% by weight to 0.05% by weight of a cationic surfactant that is 2-pyrrolidone-5-carboxylic acid (PCA) ethyl cocoyl arginate;

0.05% by weight to 2% by weight of an emulsifier that is a poly(oxyethylene) hydrogenated castor oil that has an average molar number of ethylene oxide units added of 35 to 100 moles; and 0.1% by weight to 0.3% by weight of a thickener that is a non-ionic polymer.

18. The method of claim 17, wherein the emulsifier is PEG-60 hydrogenated castor oil, and the thickener is hydroxyethylcellulose, and wherein the composition includes 0.05% by weight to 0.1% by weight CPC, 0.005% by weight to 0.02% by weight PCA ethyl cocoyl arginate, 0.1% by weight to 0.5% by weight PEG-60 hydrogenated castor oil, and 0.1% by weight to 0.2% by weight hydroxyethylcellulose.

* * * * *